United States Patent [19]

Sugimoto et al.

[11] Patent Number: 4,855,034
[45] Date of Patent: Aug. 8, 1989

[54] GAS SENSOR FOR SULFUR DIOXIDE

[75] Inventors: Eisuke Sugimoto, Niihama; Yoshiyasu Tanizawa, Wakayama; Zensaku Kozuka, Osaka, all of Japan

[73] Assignee: NGK Spark Plug Co., Ltd., Aichi, Japan

[21] Appl. No.: 474,882

[22] Filed: Mar. 14, 1983

[30] Foreign Application Priority Data

Jun. 8, 1982 [JP] Japan ................................ 57-98374

[51] Int. Cl.$^4$ ............................................. G01N 27/46
[52] U.S. Cl. .................................... 204/427; 204/424; 204/1 T
[58] Field of Search ................ 204/1 S, 1 F, 421–429; 429/33, 193

[56] References Cited

U.S. PATENT DOCUMENTS

| 3,475,223 | 10/1969 | Kummer et al. | 429/33 |
| 4,082,826 | 4/1978 | Iijima | 429/193 |
| 4,085,023 | 4/1978 | Fray | 204/1 S |
| 4,151,235 | 4/1979 | May et al. | 429/193 |
| 4,182,667 | 1/1980 | Dobson et al. | 204/1 A |
| 4,377,460 | 3/1983 | Hirayama | 204/1 S |
| 4,388,155 | 6/1983 | Chamberland et al. | 204/427 |
| 4,391,690 | 7/1983 | Lin et al. | 204/1 F |
| 4,407,912 | 10/1983 | Virkar et al. | 429/193 |

OTHER PUBLICATIONS

Yung-Fang Yu Yao and J. T. Kummer, Ion Exchange Properties of and Rates of Ionic Diffusion in Beta-Alumina, J. Inorg. Nucl. Chem., 1967, vol. 29, pp. 2453–2475.

Primary Examiner—T. Tung
Attorney, Agent, or Firm—Wegner & Bretschneider

[57] ABSTRACT $SO_2$ concentration is measurable by a gas sensor having a solid electrolyte of beta-alumina. A beta-alumina pellet may be laminated with $Na_2SO_4$ pellets on the both sides.

7 Claims, 3 Drawing Sheets

GAS SENSOR FOR SULFUR DIOXIDE

FIELD OF THE INVENTION

The present invention relates to a gas sensor for measuring the concentration of sulfur dioxide and, more particularly, to a gas sensor for sulfur dioxide which excels in heat resistance and durability and, hence, can stand up to practical use.

BACKGROUND

The measurement of the concentration of $SO_2$ in gases is required not only for the purpose of preventing environmental pollution, but also provides important information for controlling the refining process of nonferrous metals, particularly smelting sulfides thereof. It has recently been found that the concentration of $SO_2$ in a gas mixture can be determined by making use of a concentration cell in which a solid electrolyte of sulfates is used. The solid electrolytes used include potassium sulfate ($K_2SO_4$) and sodium sulfate ($Na_2SO_4$). Due to their poor heat resistance, durability and workability, such solid electrolytes can only be applied to gas sensors on a laboratory scale, and cannot be used practically for industrial applications such as smelting of nonferrous metals. Difficulties are also encountered in the industrial manufacturing of gas sensors from these electrolytes.

SUMMARY OF THE DISCLOSURE

Accordingly, it is an object of the present invention to provide a novel gas sensor for measuring sulfur dioxide gas concentration.

It is another object of the present invention to provide a sulfur dioxide gas sensor having good heat resistance and durability.

It is a further object of the present invention to provide a sulfur dioxide gas sensor having good response properties.

Still further objects of the present invention will become apparent in the disclosure, claims and accompanying drawings.

In an intensive effort to produce a gas sensor for $SO_2$ which has improved or increased heat resistance and durability and can stand up to practical use, it has been discovered that a gas sensor for $SO_2$, easy to industrially manufacture and resistant to industrial use, can be realized by making use of beta-alumina which has heretofore been used, as a highly conductive solid electrolyte for $Na^+$ ions, for the measurement of $Na^+$ ion concentration or for cells in which $Na^+$ ions participate, and whose potential applicability for that $SO_2$ gas sensor has been left out of consideration whatsoever. The present invention underlies such findings.

The present invention essentially provides a sensor for the measurement of the concentration of a sulfur dioxide gas component based on the electromotive force generated depending upon a difference in the concentration of the gas component between a gas and a reference material both coming into contact with a solid electrolyte, characterized in that said solid electrolyte is beta-alumina ($\beta$-alumina). It is noted that the term "beta-alumina" here refers to a compound of sodium oxide ($Na_2O$) with aluminium oxide ($Al_2O_3$) in a ratio approximately ranging 1:11–1:5. Namely, the beta-alumina essentially may be represented by the formula $Na_2O \cdot x\, Al_2O_3$ wherein x approximately ranges from 5 to 11.

Beta-alumina suitable for use as the solid electrolyte in the $SO_2$ gas sensor has a transference number of $Na^+$ ions of about 1, preferably 0.998 or greater, and has electron blocking properties obtainable by sintering, and, preferably, suitable heat treatment.

This beta-alumina belongs to a class superior in hardness, toughness, bending strength, tensile strength, heat resistance and wear resistance to other solid electrolytes such as sintered masses of $Na_2SO_4$ or $K_2SO_4$.

Including beta-alumina as its solid electrolyte which is an essential part of the gas sensor, the sensor according to the present invention is easy to handle, and can satisfactorily be used as a practical sensor in the industrial fields such as smelting of nonferrous metals, since the beta-alumina has a melting point of about 2000° C. by far higher than 884° C. or 1069° C., the melting point of $Na_2SO_4$ or $K_2SO_4$, and is more resistant to humidity as compared with $Na_2SO_4$ or $K_2SO_4$. The beta-alumina is now manufactured on an industrial scale, and complies with demand.

PREFERRED EMBODIMENTS OF THE DISCLOSURE

Beta-alumina includes so-called types of $\beta$-$Al_2O_3$, $\beta'$-$Al_2O_3$ and $\beta''$-$Al_2O_3$, wherein $\beta'$-$Al_2O_3$ usually is not found due to its unstable nature. Thus beta-alumina practically consists of $\beta$-$Al_2O_3$ (x=9–11), $\beta''$-$Al_2O_3$ (x=5–7) or a mixture thereof.

The term "beta-alumina" also encompasses a composition that includes a minor amount of a compound providing mono- or divalent metal ions such as $Li_2O$, $MgO$, $ZnO$, $NiO$, $MnO$ or a mixture thereof, or the like. Those metal oxides may be present in an amount of up to 3 parts by weight based on 100 parts by weight of the sum of $Na_2O$ and $Al_2O_3$.

Preferred beta-alumina is, e.g., one as disclosed in U.S. Pat. No. 4,082,826 as assigned to the same assignee of the present invention, under the provision that the compounds providing mono- or divalent metal ions as hereinabove mentioned are not used since for the purpose of the gas sensor such high ion conductivity as disclosed in U.S. Pat. No. 4,082,826 is not necessary. The entire disclosure of U.S. Pat. No. 4,082,826 is being herewith incorporated in this specification particularly with respect to the manufacturing process of beta-alumina ($\beta$-alumina) and the scope of the term of beta-alumina subject to the provision aforementioned.

The solid electrolyte is usually obtainable as a pellet in a platelet form, the pellet being either a beta-alumina platelet or a laminate platelet comprising beta-alumina laminated on both sides thereof with sodium sulfate. The sodium sulfate is obtainable as a compact, a calcined compact or a sintered body.

The solid electrolyte is provided with electrodes and a catalyst, preferably of the same material for avoiding any thermal electromotive force. The catalyst encompasses Pt, Pd or Pt-Pd alloy which are capable of accelerating the reaction of $SO_2$ with oxygen depending upon the temperature. Such catalysts contribute to quick response properties of the gas sensor. The catalyst should be present in the vicinity of the solid electrolytes preferably in fabric, granular or porous state allowing the gas to flow in contact with the catalyst. The catalyst may act as an electrode so far as it contacts with the surface of the solid electrolyte.

The laminate solid electrolyte may be obtained by tightly contacting sodium sulfate with beta-alumina. The thickness of the beta-alumina platelet generally depends upon pressure to be applied thereon, structure of the gas sensor or other conditions of design and application. However, it may be, e.g., 1 to 3 mm or thicker or, thinner if desired.

The reference material may be a gas containing a given amount of $SO_2$.

In the following the preferred embodiments will be described in detail with reference to the accompanying drawings which, however, are not presented for limitation of the present invention. Any modification obvious in the art may be taken within the concept and claimed scope of the present invention.

Figure 1:
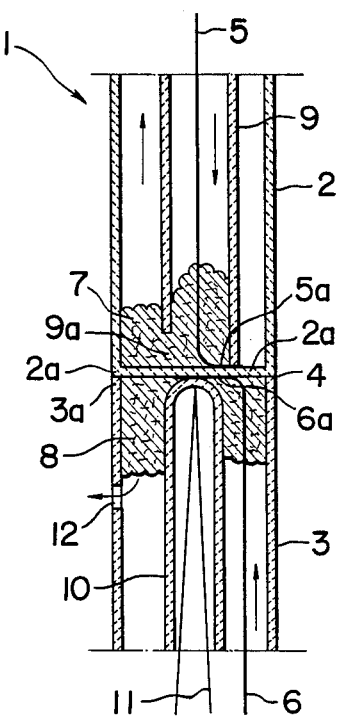
FIG. 1 is a longitudinal sectional view showing part of a first embodiment of the gas sensor for sulfur dioxide according to the present invention.

Referring to the drawings, particularly to FIG. 1, there is shown a first embodiment of the gas sensor for sulfur dioxide ($SO_2$) according to the present invention. Reference numeral 1 stands generally for a gas sensor for $SO_2$, 2 a cylindrical tube of beta-alumina having a closed end wall 2a, and 3 an alpha-alumina tube with the same diameter but without any closed end wall. These tubes 2 and 3 are sealed together at the junction 4 of their closed end 2a and open end 3a with the aid of heat-resistant glass.

The beta-alumina tube 2 includes a gas inlet pipe 9 of alpha-alumina with its lower end being in contact with beta-alumina and partly opened at 9a. At and around the gas outlet 9a there is filled platinum wool 7 as a catalyst in such a manner that the outlet 9a is entirely embedded therein. A platinum lead 5 is inserted into the platinum wool 7 through the gas inlet pipe 9 with its lower end portion being bent parallel with the closed end wall 2a and brought into close contact with the closed end wall to define an electrode 5a. The platinum wool also acts as a part of electrode. Into the alpha-alumina tube 3 is inserted a thermocouple 11 of platinum/platinum rhodium for temperature measurement, which is further disposed in a protective pipe 10 of alpha-alumina for insulation from other portions and parts. The upper end portion of the pipe 10 is filled with platinum wool 8 in such a manner that it entirely covers the surface of the closed end wall 2a of the beta-alumina tube 2. Between the alpha-alumina tube 3 and the protective pipe 10 is inserted a platinum lead 6 with its upper end portion being bent parallel with the closed wall 2a and brought into close contact therewith to define an electrode 6a. The platinum wool acts as a part of electrode as well. In the vicinity of the closed end wall 2a, the side wall of the alpha-alumina tube 3 is provided with a gas discharge outlet 12 to be in communication with the open air. The electrodes 5a and 6a may either be in contact with the closed end wall 2a, or be fixed thereto by metallizing with a platinum paste, which is a common manner for the attachment of electrodes to solid electrolytes.

In the gas sensor arrangement for $SO_2$ as explained above, the end wall side directed to the beta-alumina tube 2 may serve as a reference electrode, and the other end wall side directed to the alpha-alumina tube 3 as a sample electrode. The concentration of $SO_2$ in a sample gas admitted into the sample electrode can then be determined as a function of an electromotive force generated between the individual electrodes 5a and 6a by the introduction of a reference gas into the reference electrode. For instance, the reference gas used may be a gas mixture containing 9740 ppm of $SO_2$ balanced with air. This gas mixture enters from the upstream side of the inlet pipe 9 into the platinum wool 7, and is discharged through a double shell space between the beta-alumina tube 2 and the inlet pipe 9 through the wool 7.

On the other hand, the sample gas passes through a space between the alpha-alumina tube 3 and the protective pipe 10 having the thermocouple 11 inserted therein, enters the platinum wool 8, and is discharged from the gas outlet 12 through the wool 8.

In this process, a concentration cell is produced as follows:

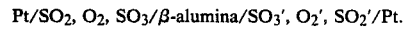

Pt/$SO_2$, $O_2$, $SO_3$/$\beta$-alumina/$SO_3'$, $O_2'$, $SO_2'$/Pt.

The electromotive force is considered to be generated due to $Na_2SO_4$ formed on the surface of beta-alumina. Since the transference number of $Na^+$ ions is 1 in the solid electrolyte of beta-alumina, the electromotive force of the above-mentioned cell may be expressed by the equation 1.

$$E = (RT/F)\ln(\alpha'_{Na}/\alpha_{Na}) \quad (1)$$

Wherein
E is electromotive force,
R is the gas constant,
T is absolute temperature,
F is Faraday constant, and
$\alpha'_{Na}$ and $\alpha_{Na}$ are the activity of Na on the individual electrode sides.

From the equilibrium relationship of the reaction shown by Eq. 2, Eq. 1 may be reduced to Eq. 3. From the equilibrium relationship of the reaction shown by Eq. 4 may also be reduced to the form of Eq. 5.

$$Na_2SO_4 = 2Na + SO_3 + \tfrac{1}{2}O_2 \quad (2)$$

$$E = (RT/2F)\ln[(P_{O_2})^{\frac{1}{2}} \cdot P_{SO_3}/(P_{O_2}')^{\frac{1}{2}} \cdot P_{SO_3'}] \quad (3)$$

$$SO_3 = SO_2 + \tfrac{1}{2}O_2 \quad (4)$$

$$E = (RT/2F)\ln(P_{O_2} \cdot P_{SO_2}/P_{O_2}' \cdot P_{SO_2'}) \quad (5)$$

In equations 3-5 inclusive, symbols $P_{O_2}$, $P_{O_2}'$, $P_{SO_3}$, $P_{SO_3}'$, $P_{SO_2}$ and $P_{SO_2}'$ stand for the equilibrium partial pressures of the individual components at the individual electrodes.

As the concentration of $SO_2$ in the gas mixture is as low as below 1%, and balanced with air in this embodiment, the equilibrium partial pressure of oxygen at the individual electrodes is taken as being approximately 0.21 atm. and kept constant at that pressure. Hence, Eq. 5 may be reduced to the form of Eq. 6.

$$E = (RT2F)\ln(P_{SO_2}/P_{SO_2'}) \quad (6)$$

With Eq. 6, it is possible to calculate the concentration of $SO_2$ in the sample gas, given the electromotive force (E) and the concentration (partial pressure) of $SO_2$ in the reference gas at one electrode.

Figure 2:
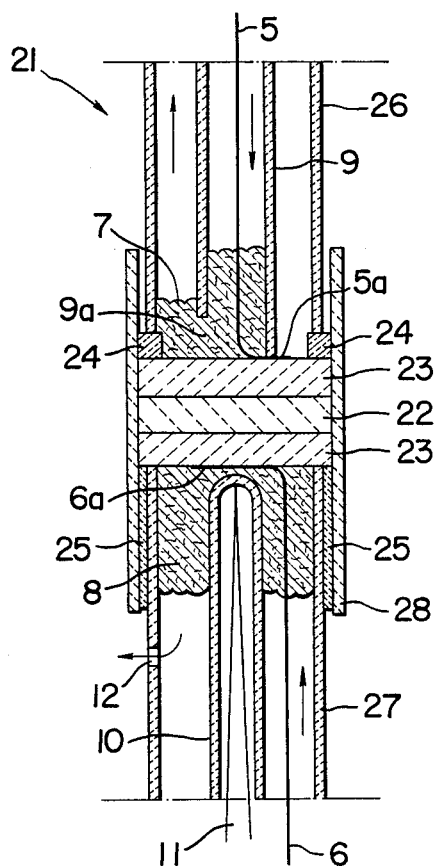
FIG. 2 is a longitudinal, sectional view showing part of a second embodiment of the present invention.

While the present invention has been described with reference to the first embodiment as illustrated in FIG. 1, it may, for example, be modified to a second embodiment as depicted in FIG. 2.

In FIG. 2, reference numeral 21 denotes generally a second gas sensor for $SO_2$ according to the present invention, 22 a beta-alumina pellet(platelet), and 23 $Na_2SO_4$ pellets.

The beta-alumina pellet is laminated on both its sides with two $Na_2SO_4$ pellets to form a three-layer solid electrolyte structure as one piece, which is to be fixedly inserted substantially in the vicinity of the center of an alpha-alumina outer cylinder 28.

An alpha-alumina tube 26 is with its end fixedly sealed onto the surface of one $Na_2SO_4$ pellet 23 of the three-layer solid electrolyte structure with the aid of a heat-resistant glass seal 24.

The alpha-alumina tube 26 includes a gas inlet pipe 9 of alpha-alumina with its lower end being into contact with the surface of one $Na_2SO_4$ pellet 23 and partly opened at 9a. At and around the outlet opening 9a there is charged with catalytic platinum woll 7 in such a manner that the opening 9a is entirely embedded therein. Into the platinum wool 7, a platinum lead 5 is inserted through the inlet pipe 9 with its lower end portion being bent parallel with the surface of the said one pellet 23 and brought into close contact therewith to define an electrode 5a. The platinum wool 7 acts as a part of the electrode as well.

An alpha-alumina tube 27 has its upper end bought into contact with the surface of the other $Na_2SO_4$ pellet 23 positioned opposite to the said one pellet 23 having the alumina tube 26 sealed onto its surface. The upper end portion of the tube 27 is bonded and fixedly sealed onto the inner surface of the outer sylinder 28 by means of alumina cement 25. Like the first embodiment, a thermocouple 11 is inserted into the alpha-alumina tube 27 for temperature measurement, and disposed in a protective pipe 10 of alpha-alumina pipe for insulation from other portions and parts. Around the upper end portion of the pipe 10 platinum wool 8 is charged in such a manner that it covers entirely the surface of the other $Na_2SO_4$ pellet 23. A platinum lead 6 is inserted between the alpha-alumina tube 27 and the protective pipe 10 with its upper end portion being bent parallel with the surface of the other pellet 23 and brought into close contact therewith to define an electrode 6a. In the vicinity of the other pellet 23, the side wall of alpha-alumina tube 27 is provided with a gas discharge opening 12 which communiate with the open air. Like the first embodiment, the electrodes 5a and 6a may either be in contact with the $Na_2SO_4$ pellets 23, or be fixed thereto by metallizing with a platinum paste.

In the gas sensor arrangement for $SO_2$ as explained above, the alumina tube 26 may serve as a reference electrode, and the alpha-alumina tube 27 as a sample electrode. The concentration of $SO_2$ in a sample gas admitted onto the sample electrode can be determined as a function of an electromotive force generated between the individual elelctrodes 5a and 6a by the introduction of a reference gas onto the reference electrode. As in the first embodiment, the reference gas used may be a gas mixture balanced with air and containing 9740 ppm $SO_2$. This gas mixture enters from the upstream side of the inlet pipe 9 into the platinum wool 7, and is discharged through a space between the alumina tube 26 and the inlet pipe 9 via the outlet opening 9a.

On the other hand, the sample gas passes between the alpha-alumina tube 27 and the protective tube 10 having the thermocouple 11 inserted therein, enters the platinum wool 8, and is discharged through the gas outlet opening 12 flowing throughout the wool 8.

In this process, a concentration cell is produced as follows:

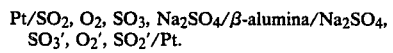

Pt/$SO_2$, $O_2$, $SO_3$, $Na_2SO_4$/$\beta$-alumina/$Na_2SO_4$,
$SO_3'$, $O_2'$, $SO_2'$/Pt.

Although the foregoing equation 6 also theoretically holds for the second embodiment, the concentration of $SO_2$ may be determined by appropriate correction, since the measured values are higher than the theoretical by about 7-8 mV. However, the period of time during which equilibrium is reached is about 30 minutes in the first embodiment, whereas it is only about 5 minutes in the second embodiment. Thus, the second embodiment is preferable in view of time for measurement.

The present invention will now be elucidated further with reference to the following, non-restrictive example showing the results of experiments with the gas sensors made according to the teachings of the present invention.

EXAMPLE 1

A cylindrical crucible of $\beta$-alumina, 10 mm in outer diameter, 7 mm in inner diameter and 100 mm in length, (manufactured by NGK Spark Plug Co., Ltd.), was used as the cylindrical beta-alumina tube 2 having its end wall of 1.5 mm thick closed at 2a. An alpha-alumina tube having the same diameters and length was used as the alpha-alumina tube 3 having no closed end wall. These tubes were assembled into the gas sensor 1 according to the first embodiment, by which the concentration of $SO_2$ was measured. For the reference electrode was used a gas mixture balanced with air and having a $SO_2$ content of 9740 ppm, and for the sample electrode gas mixtures balanced likewise with air and having various $SO_2$ contents.

Figure 3:
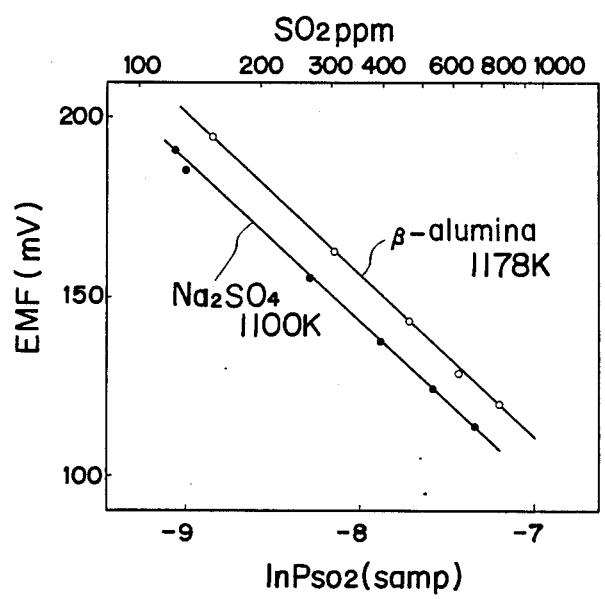
FIG. 3 is a graphical view illustrative of the relationship between the concentration of $SO_2$ and the electromotive force in the first embodiment.

FIG. 3 illustrates the relationship between the values found for electromotive forces and the equilibrium concentration of $SO_2$ on the sample electrode, both measured at 1178K. In FIG. 3, the linear curve indicates the theoretical values calculated from Eq. 6, and open circles the values obtained as regards beta-alumina. From this graphical view, it has been ascertained that the values found for electromotive forces measured using beta-alumina, are well in conformity with the theoretical as a function of concentration, and the use of a beta-alumina solid electrolyte is constantly effective for the determination of $SO_2$ in gases. Such use and potential applicability of beta-alumina for a $SO_2$ sensor have been left out of consideration in the art whatsoever, although $\beta$-alumina has been used as a Na sensor or an electric cell.

The beta-alumina pellets have been prepared substantially in a manner as disclosed in U.S. Pat. No. 4,082,826 Iijima subject to partial modification that no compounds capable of providing metal ions such as $Li_2O$, MgO or the like have been used. The used beta-alumina pellets correspond to the Sample No. 4a of Table 1 provided that $Li_2O$ was not included, thus substantially consisting of $\beta$-$Al_2O_3$ and $\beta''$-$Al_2O_3$.

The glass seal was made at a temperature about 800° C.

FIG. 3 also shows the results of a comparative run wherein a gas sensor as disclosed in the second embodiment was applied at 1100 K, which was made by using as the solid electrolyte only the $Na_2SO_4$ pellets. In FIG. 3, another line and black circles represent respectively values found and a theoretical curve for electromotive forces measured at 1100 K. From this figure, it has also turned out that beta-alumina exhibits linearity similar to that of $Na_2SO_4$, and combines excellent physical properties with satisfactory possibility for sensors.

Figure 4:
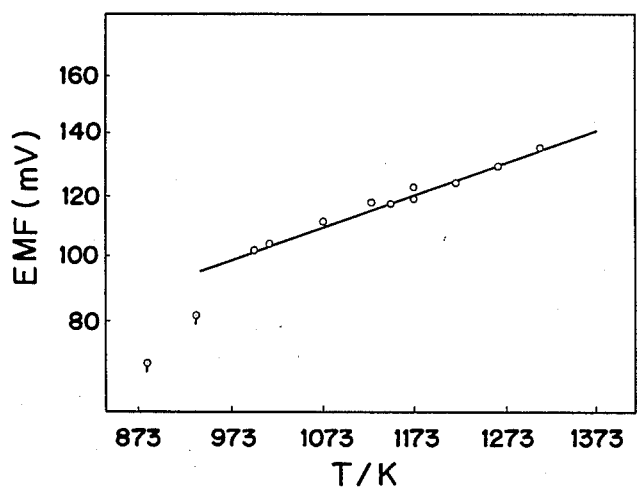
FIG. 4 is a graphic view illustrative of the relationship between the temperature and the electromotive force.

For the reference electrode was used a gas mixture balanced with air and having a $SO_2$ content of 9740 ppm, and for the sample electrode a gas mixture balanced likewise with air and having a $SO_2$ content of 920 ppm. FIG. 4 indicates the measurements for electromotive forces obtained at varied temperatures. In this figure, the line and open circles indicate the theoretical and found values, respectively. As a result, it has been found that the observed values are in well conformity with the theoretical in a temperature range above 1023 K. It is noted, however, that the period of time during which equilibrium is reached is longer as compared with the case of the $Na_2SO_4$ solid electrolyte, and is about 30 minutes.

$Na_2SO_4$ pellets in the form of a platelet was prepared by compacting, sintering at 880° C. just below the melting point thereof and polishing the cut out surface.

What is claimed is:

1. A gas sensor for the measurement of the concentration of a sulfur dioxide component of an objective gas, comprising:

a solid electrolyte consisting of beta-alumina, which solid electrode is partially exposed to the objective gas;

a reference material which produces a predetermined Na activity in the electrolyte, the electrolyte being so arranged as to separate the objective gas from the reference material; and a catalyst selected from the group consisting of Pt, Pd, Pf-Pd alloys and mixtures thereof provided at least on the portion of the electrolyte exposed to the objective gas, wherein the other side of the solid electrolyte is kept in contact with the reference material, said sensor determining sulfur dioxide concentration based upon the electromotive force generated between said sulfur dioxide component and said reference material.

2. The gas sensor as defined in claim 1, wherein beta-alumina is essentially represented by the formula $Na_2O \cdot x\, Al_2O_3$ wherein x approximately ranges from 5 to 11.

3. The gas sensor as defined in claim 2, wherein the beta-alumina essentially consists of $\beta$-$Al_2O_3$, $\beta''$-$Al_2O_3$ or a mixture thereof.

4. The gas sensor as defined in claim 1, wherein the beta-alumina has a transport number of $Na^+$ ions of approximately 1 and has electron blocking properties.

5. The gas sensor as defined in claim 1, wherein said solid electrolyte is provided with an electrode on both its sides.

6. The gas sensor as defined in claim 5, wherein said electrode is made of one material selected from the group consisting of Pt, Pd and Pt-Pd alloy.

7. The gas sensor as defined in claim 1, wherein the reference material is a gas having a predetermined $SO_2$ concentration.

* * * * *